United States Patent [19]

Mann

[11] Patent Number: 5,406,959
[45] Date of Patent: Apr. 18, 1995

[54] METHOD AND APPARATUS FOR OBTAINING AN ARTERIAL BIOPSY AND FOR DIAGNOSTING DISEASES OF THE VASCULAR SYSTEM

[76] Inventor: David Mann, 4720 Everts St., San Diego, Calif. 92109

[21] Appl. No.: 173,571

[22] Filed: Dec. 22, 1993

Related U.S. Application Data

[63] Continuation-in-part of Ser. No. 901,830, Jun. 22, 1992, Pat. No. 5,287,857.

[51] Int. Cl.$^6$ ............................................. A61B 10/00
[52] U.S. Cl. .................................................. 128/753
[58] Field of Search ............................... 128/751–754; 606/167, 170; 604/158, 164, 171

[56] References Cited

U.S. PATENT DOCUMENTS

| | | | |
|---|---|---|---|
| 3,606,878 | 9/1971 | Kellogg, Jr | 128/2 B |
| 3,830,225 | 8/1974 | Shinnick | 128/2 B |
| 3,929,126 | 12/1975 | Corsaut | 128/240 |
| 4,099,518 | 7/1978 | Baylis et al. | 128/2 B |
| 4,414,055 | 10/1983 | Simpson et al. | 29/447 |
| 4,424,833 | 1/1984 | Spector et al. | 137/849 |
| 4,465,072 | 8/1984 | Taberi | 128/348.1 |
| 4,617,940 | 10/1986 | Wang | 128/753 |
| 4,620,547 | 11/1986 | Boebel | 128/754 |
| 4,640,296 | 2/1987 | Schnepp-Pesch et al. | 128/754 |
| 4,641,654 | 2/1987 | Samson et al. | 128/344 |
| 4,649,263 | 3/1987 | Frisbie et al. | 128/344 |
| 4,681,123 | 7/1987 | Valthchev | 128/753 |
| 4,692,200 | 9/1987 | Powell | 156/289 |
| 4,693,257 | 9/1987 | Markham | 128/752 |
| 4,708,147 | 12/1987 | Haaga | 128/753 |
| 4,723,936 | 3/1988 | Buchbinder et al. | 604/95 |
| 4,762,130 | 8/1988 | Fogarty et al. | 128/348.1 |
| 4,763,667 | 8/1988 | Manzo | 128/750 |
| 4,763,668 | 8/1988 | Macek et al. | 128/751 |
| 4,781,202 | 11/1988 | Janese | 128/754 |
| 4,790,315 | 12/1988 | Mueller, Jr. et al. | 128/344 |
| 4,793,350 | 12/1988 | Mar et al. | 128/344 |
| 4,793,351 | 12/1988 | Landman et al. | 128/344 |
| 4,815,478 | 3/1989 | Buchbinder et al. | 128/772 |
| 4,832,048 | 5/1989 | Cohen | 128/786 |
| 4,844,087 | 7/1989 | Garg | 128/753 |
| 4,850,373 | 7/1989 | Zatloukal et al. | 128/749 |
| 4,867,156 | 9/1989 | Stack et al. | 128/305 |

(List continued on next page.)

OTHER PUBLICATIONS

Bauriedel et al., "Migratory Activity of Human Smooth Muscle Cells Cultivated From Coronary and Peripheral Primary and Restenotic Lesions Removed by Percutaneous Atherectomy", Circulation vol. 85, No. 2, Feb. 1992, pp. 554–564.

"Primary Pulmonary Hypertension: A Look at the Future" by John H. Newman, MD, Joseph C. Ross, MD, Sep. 1989, American College of Cardiology, pp. 551–555.

"Hypoxia-Induced Structural Changes in the Media and Adventitia of the Rat Hilar Pulmonary Artery and Their Regression", by Barbara Meyrick, PhD, and Lynne Reid, MD, Feb. 13, 1980, American Association of Pathologists, pp. 151–174.

"Pulmonary Hypertension: A Cellular Basis for Understanding the Pathophysiology and Treatment" by Stuart Rich, MD, FACC, Bruce H. Brundage MD, FACC, 1989, The American College of Cardiology, pp. 545–550.

(List continued on next page.)

*Primary Examiner*—Max Hindenberg
*Attorney, Agent, or Firm*—Stephen A. Gratton

[57] ABSTRACT

A method and apparatus for obtaining a biopsy from an artery includes the steps of: inserting a catheter into an artery, positioning the catheter at a desired location within the artery, cutting a biopsy sample from the inner surface of the artery, and withdrawing the catheter and biopsy sample from the artery with the biopsy sample protected and its orientation with respect to its parent tissue preserved. The catheter includes an inner tube coupled to a vacuum source and having a beveled opening for contacting the artery. An outer tube is slidably mounted to the inner tube and has a cutting edge which slides over and severs arterial tissue retained in the beveled opening.

20 Claims, 5 Drawing Sheets

U.S. PATENT DOCUMENTS

| | | | |
|---|---|---|---|
| 4,873,991 | 10/1989 | Skinner | 128/754 |
| 4,877,030 | 10/1989 | Beck et al. | 128/343 |
| 4,877,031 | 10/1989 | Conway et al. | 128/344 |
| 4,877,037 | 10/1989 | Ko et al. | 128/756 |
| 4,887,613 | 12/1989 | Farr et al. | 606/159 |
| 4,903,709 | 2/1990 | Skinner | 128/754 |
| 4,925,450 | 5/1990 | Imonti et al. | 604/240 |
| 4,932,959 | 6/1990 | Horzewski | 606/194 |
| 4,953,559 | 9/1990 | Salerno | 128/751 |
| 4,961,430 | 10/1990 | Sheahon | 128/754 |
| 5,006,113 | 4/1991 | Fischer | 604/167 |
| 5,011,490 | 4/1991 | Fischell et al. | 606/159 |
| 5,188,605 | 2/1993 | Sleep | 604/158 |

OTHER PUBLICATIONS

"Proceedings of National Heart, Lung, and Blood Institute Pediatric Cardiology Workshop: Pulmonary Hyerptension" by William F. Freidman, 1986, International Pediatric Research Foundation, Inc.

"The Prevalence of Pulmonary Hypertension in the United States", Stuart Rich, M.D., F.C.C.P., Eva Chomka, MD, Lawrence Hasara, MD, Kimberly Hart, RN, Terence Drizd, B. S., Esther Joo, MPH and Paul S. Levy, Sc.D., Oct. 17, 1988. pp. 236–241.

"Cardiac Diagnostic and Treatment" by Fowler 2nd Ed. Harper & Row, 1980.

"Cardiology: Fundamentals and Practice" by Robert O. Brandenburg, MD, Valentin Fuster, MD, Emilio R. Giuliani, MD, Dwight C. McGoon, MD.

"The Journal of Pediatrics" by Ronald M. Perkin, MD and Nick G. Anas, MD, Oct., 1984, pp. 511–515.

"Flexible Myocardial Biopsy Forceps" by William Cook, 1989.

"Put Out Diamonds in the Rough" *Introducing Rotablator*, 1990.

"Simpson Peripheral AtheroCath" Preparation and Procedure. 1988.

"Simpson Peripheral AtheroCath" Design, 1989.

METHOD AND APPARATUS FOR OBTAINING AN ARTERIAL BIOPSY AND FOR DIAGNOSING DISEASES OF THE VASCULAR SYSTEM

CROSS REFERENCE TO RELATED APPLICATIONS

This application is a continuation-in-part of U.S. patent application Ser. No. 07/901,830 filed on Jun. 22, 1992 and entitled "Apparatus and Method For Obtaining An Arterial Biopsy", U.S. Pat. No. 5,287,857.

FIELD OF THE INVENTION

This invention relates to medical technology and particularly to medical surgical and diagnostic procedures. More specifically, the present invention relates to a method and apparatus for obtaining a biopsy sample from the inner surface of an arterial wall for use in the diagnosis, treatment and study of vascular diseases.

BACKGROUND OF THE INVENTION

Vascular diseases, and complications arising from vascular diseases, are a leading cause of death in modern society. Medical science therefore, is increasingly concerned with the diagnosis and treatment of these types of diseases. Recently many new techniques have been developed in this area.

As an example, angioplasty is a medical procedure in which an inflatable balloon is used to widen a narrowed or stenotic segment of an artery. As another example, atherectomy is a medical procedure in which plaque in an obstructed artery is cut away and removed from the artery.

FIGS. 1A, 2A and 3A illustrate some different arterial conditions that may occur in a vascular system of a living person. FIG. 1A is a longitudinal cross section of a normal healthy artery 10. The healthy artery 10 includes a main branch 12 which bifurcates into two smaller branches 14, 16. A lateral cross section of the healthy artery 10 is shown in Figure 1B. The healthy artery 10 is formed of three distinct layers. An inner layer 18 (or intima) of the artery 10 consists of a layer of elastic tissue on whose inner surface rests a layer of plate-like endothelial cells. A middle layer 20 (or media) of the artery 10 consists of smooth muscle cells. An outer layer 22 (or adventitia) consists of fibrous tissue. An arterial lumen 24 provides a conduit for blood flow. In a healthy artery 10 this lumen 24 is clear and unobstructed. In addition, the healthy artery 10 is highly elastic, dilating at each heart-beat as blood is driven into it.

FIG. 2A illustrates an arterial condition referred to as point stenoses, which could be caused by atherosclerosis. An atherosclerotic artery 26 is often characterized by obstructive tissue 28 (e.g. atheromous plaque) which forms in the lumen 24 of the artery 26. The obstructed segments 30, 32 of the artery 26 are referred to as stenotic segments and are characterized by a localized narrowing. In atherosclerosis, the obstructive tissue 28 is called plaque, and is typically formed of a fatty substance such as cholesterol. This obstructive tissue 28 builds up on the inner layer 20 of the atherosclerotic artery 26 and has an inelastic quality. The obstructive tissue 28 also tends to clog the lumen 24 of the artery 26 and impairs blood circulation.

As the obstructive tissue 28 in an atherosclerotic artery 26 grows larger, the lumen 24 of the artery 26 becomes smaller. In due course the lumen 24 of the artery 26 may be so narrowed that it becomes blocked. If this occurs in the coronary arteries the result is a coronary thrombosis, commonly known as a heart attack. If it occurs in the brain it causes a stroke. The cause of atherosclerosis is not known, but one factor is the consumption of excessive saturated fats. Another contributing factor in plaque development is believed to be the migration of smooth muscle cells (SMCs) across the vascular wall.

FIG. 3A illustrates another condition of the arteries known as hypertension. FIG. 3A is characterized by a generalized stenosis. Generalized stenotic arteries 34 are characterized by a generalized thickening of the arterial wall 138. The exact cause of this thickening is often unknown. Generalized stenosis of the arteries 34 is often associated with a decreased lumen 24 in the affected areas. The thickening of the arterial wall 138 can be due to a variety of factors including cells that grow larger in size (hypertrophic) cells, cells that multiply (proliferation), neoplasms, bacterial conglomerations, inflammatory cells, virally infected cells or other causes. The arterial wall 138 can have different characteristics depending on the factors responsible for the narrowing. In generalized stenotic arteries 34, the thickened arterial wall 138 can be elastic or inelastic depending on the nature of the underlying disease.

One well known medical procedure for diagnosing and treating certain diseases involves obtaining a biopsy sample of the afflicted area. Medical devices for obtaining a biopsy of different body structures such as the heart, muscles, intestines, and the uterus are well known in the art. As an example, a medical instrument known in the art as a Schulz-Caves bioptome is an endomyocardial biopsy device for removing a biopsy sample from the heart. In general, even though biopsy instruments are well known in the art, there are no prior art biopsy instruments specifically adapted for obtaining biopsy samples from the inner surface of an artery.

Some medical instruments, such as atherocatheters, are designed to break-up and remove obstructive tissue from a stenotic segment of an artery. U.S. Pat. No. 5,011,490 to Fischell is representative of this type of instrument. Atherocatheters, however, are not specifically designed to retrieve a tissue sample other than obstructive tissue (e.g. atheroma). This is because atherocatheters are designed to remove obstructive tissue which is inelastic, and to avoid healthy arterial tissue, which is elastic. These devices will therefore not function to retrieve any tissue other than an inelastic obstruction occurring at a stenotic segment of an artery. In addition, any tissue retrieved is entrained in blood making it difficult to isolate.

The present invention recognizes that in some instances it may be desirable to obtain a sample of arterial tissue which is not a part of a point stenosis. This may be healthy arterial tissue or diseased arterial tissue located at a segment of the artery having generalized or localized narrowing. As an example, in the past it has not been possible to obtain samples of the fragile endothelial cell layer that lines the inner surface of the artery. (See for instance the article by Bauriedel et al., entitled "Migratory Activity of Human Smooth Muscle", Circulation February 1992:85:2:554–564). The present invention also recognizes that it is desirable to retrieve a biopsy sample which is undamaged, isolated from blood and in an optimal condition for examination.

Information gained from the study of such arterial tissue may be useful in determining the cause and treatment of various cardiovascular maladies. As an example, millions of people suffer from what is called essential hypertension. This hypertension is deemed essential because there is no known cause, let alone cure, for it. The current treatment for hypertension entails prescribing drugs that reduce blood volume or relax blood vessels. While these medicines help control hypertension, this treatment does not cure hypertension, nor shed any light on the underlying causes of high blood pressure.

There are many different forms of hypertension, and they are characterized by a wide variety of symptoms and physiological changes. Hypertension can be caused by or be the cause of narrowing in the arteries. This narrowing can be systemic and generalized as in pulmonary hypertension, or localized into a point stenoses as in a concentration of atheromous plaque. Viral, bacteriological, oncological and inflammatory causes have also been postulated as causes of arterial hypertension, but until now there has been no procedure to sample tissues from areas other than localized stenoses.

Much of the effort and technological development of catheter systems that constitute the prior art has been concerned with dilating or eliminating point stenoses. Any sampling function performed is an added bonus. The prior art devices are not designed primarily for the purpose of taking a biopsy, nor do they perform in any other than highly specific conditions, namely, arteries with point stenoses.

In view of these and other shortcomings of the prior art, it is an object of the present invention to provide a method and apparatus for obtaining a biopsy sample from the inner surface of an arterial wall at an arterial segment without a localized stenoses. It is a further object of the present invention to provide a method and apparatus for obtaining a biopsy sample from the inner surface of an artery while minimizing trauma to the artery and to the biopsy sample.

It is yet another object of the present invention to provide a method and apparatus for obtaining a biopsy sample in which the orientation of the biopsy sample relative to the parent tissue is preserved. It is still another object of the present invention to provide a method and apparatus for obtaining a biopsy sample from an artery of a living being in which the risk of damage or puncture to the arterial wall is minimized.

It is a further object of the present invention to provide a method and apparatus for obtaining an endoarterial tissue sample that contains endothelial cells. It is a still further object of the present invention to provide a method and apparatus for obtaining a biopsy sample from an artery that includes one or more of the following constituents: smooth muscle cells, adventitia cells, thickened cells, hypertrophic cells, neoplastic tissue, bacterial conglomerations, virally infected cells, inflammatory cellular components, or cells containing exogeneously introduced recombinant genetical material.

SUMMARY OF THE INVENTION

In accordance with the present invention a method and apparatus for obtaining a biopsy sample from an artery are provided. The method of the invention includes the steps of: inserting a catheter into the artery; positioning the catheter at a desired location within the artery; contacting an inside surface of the artery using a vacuum directed through an opening formed in the catheter; cutting a biopsy sample from the arterial wall; and then removing the catheter with the biopsy retained therein.

The catheter of the invention is adapted to mechanically cut a sample of tissue from the inner surface of the arterial wall without puncturing the artery and then to remove the sample from the artery with little or no damage to the sample. The catheter is formed with an inner tube having a beveled opening for contacting the inner surface of the artery. An outer tube is slidably mounted on the inner tube and has a cutting edge adapted to slide over the beveled opening. Upon placement of the catheter within the artery, a segment of tissue from the inner surface of the artery is held in the beveled opening using a vacuum directed through the inner tube. An operator by manipulating the inner and outer tubes moves the cutting edge of the outer tube over the retained tissue to sever the tissue from the artery and form the biopsy sample. This biopsy sample is then retained and protected within the beveled opening as the catheter is withdrawn from the artery.

Handles are attached to both the inner tube and the outer tube for manipulating the tubes through the artery and for moving the cutting edge of the outer tube over the tissue sample retained on the inner tube. A moveable sleeve is placed over the outer tube to provide a reduced friction passage for the outer tube relative to an introducer sheath during the cutting step of the procedure.

The inner tube includes a closed tip portion at a distal end wherein the beveled opening is formed. The size and depth of the beveled opening can be selected to contact and remove different layers of the artery having different cellular components. Small and shallow beveled openings produce biopsy specimens that contain the innermost cellular components, primarily endothelial and smooth muscle cells. Larger and deeper beveled openings produce biopsy specimens that contain deeper cellular components, such as adventitia cells.

The outer tube includes a sharpened circumferential edge at its distal end which forms the cutting edge of the catheter. By moving the outer tube relative to the inner tube an operator moves the cutting edge over the beveled opening. A sample thus cut is held and protected in the beveled opening by the outer tube. Upon withdrawal of the catheter from the artery, the biopsy sample is removed from the beveled opening by retracting the outer tube relative to the inner tube. During this procedure the orientation of the biopsy sample relative to the parent tissue is preserved.

The biopsy sample can then be examined histologically, grown in cell cultures, or used as a source of cellular material. In addition, the method and apparatus of the invention can be used for obtaining biopsy samples for the purpose of obtaining genetic information and material, or to sample exogenously introduced recombinant genetic material. Moreover, the biopsy samples may include soft tissue structures lining the arterial walls such as hypertrophied tissue, neoplasms, bacteria, thickened tissue, virally infected cells, and other inflammatory cellular components.

Various objects, advantages and capabilities of the present invention will become more apparent from the following more particular description of the preferred embodiments of the invention as illustrated in the accompanying drawings.

DETAILED DESCRIPTION OF THE PREFERRED EMBODIMENTS

Figures 3A, 3B:
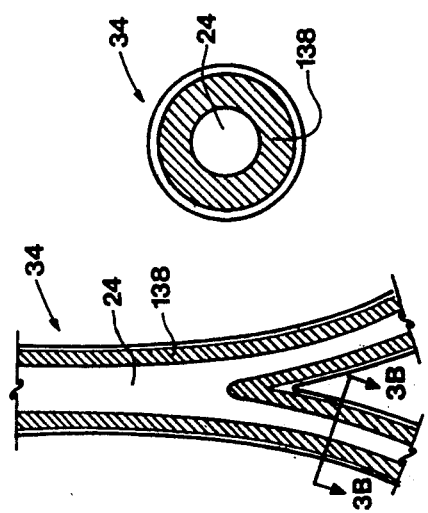
FIG. 3A is a longitudinal cross section of an artery having a generalized narrowing.
FIG. 3B is a cross section taken along section line 3B—3B of FIG. 3A.
Figures 2A, 2B:
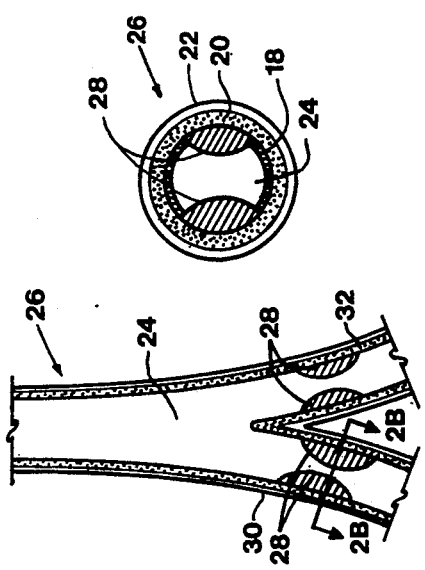
FIG. 2A is a longitudinal cross section of an artery having obstructive tissue which forms a point stenoses.
FIG. 2B is a cross section taken along section line 2B—2B of FIG. 2A.
Figures 1A, 1B:
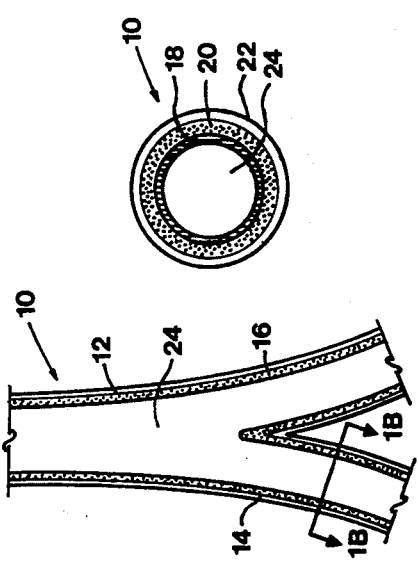
FIG. 1A is a longitudinal cross section of a normal healthy artery.
FIG. 1B is a cross section taken along section line 1B—1B of FIG. 1A.
Figure 4:
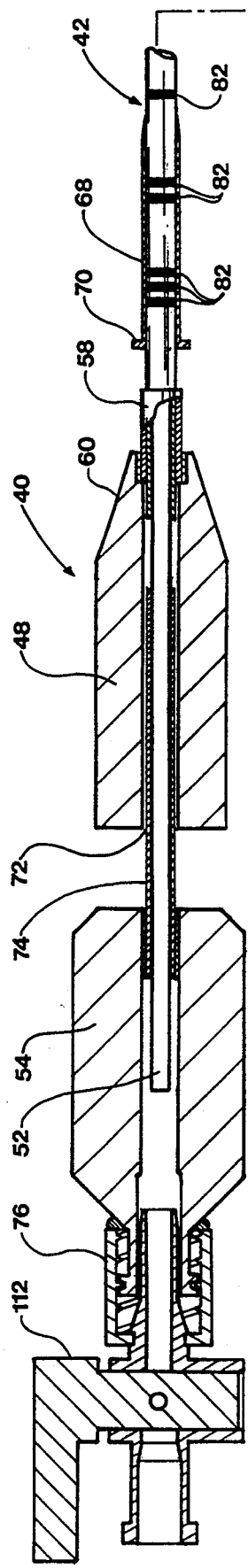
FIG. 4 is a cross-sectional view of a biopsy catheter constructed in accordance with the present invention.
Figure 4:
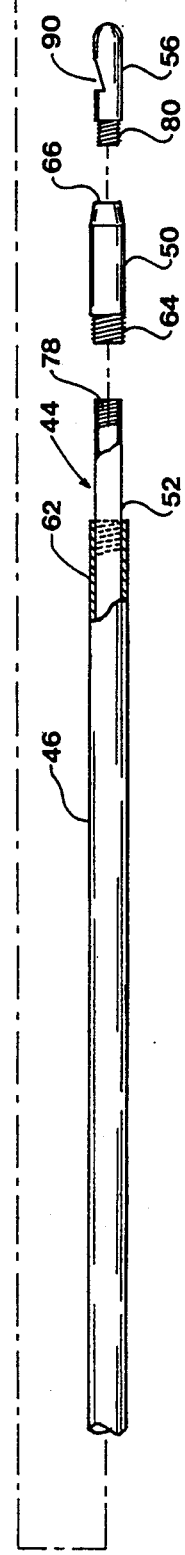

Referring now to FIG. 4, a biopsy catheter constructed in accordance with the invention is shown and generally designated as 40. The biopsy catheter 40 must be sterilized before it comes in contact with a patient 140 (FIG. 10) and is intended for use in a sterile area such as an operating room. The biopsy catheter 40 includes an outer tube assembly 42 and an inner tube assembly 44. The outer tube assembly 42 includes an outer tube 46, an outer tube handle 48, and a cutter tip 50. The inner tube assembly 44 includes an inner tube 52, an inner tube handle 54, and suction tip 56.

The outer tube 46 is formed of a length of flexible tubing of a polymeric material such as polyterafluroethylene, nylon, or polyurethane. The outer tube 46 is sized with an outside diameter that will pass freely through an artery of a human being and with a length that will allow access to an arterial site within the body. In addition, the outer tube 46 must be flexible enough to bend through the tortuous path of an artery yet rigid enough to transmit compressive and tensile forces linearly from the outer tube handle 48 to the cutter tip 50.

Figure 5:
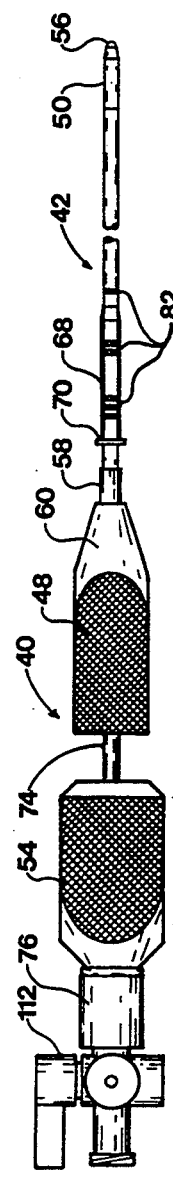
FIG. 5 is a side elevation view of a biopsy catheter constructed in accordance with the present invention shown with a cutting portion of the catheter protected.
Figure 6:
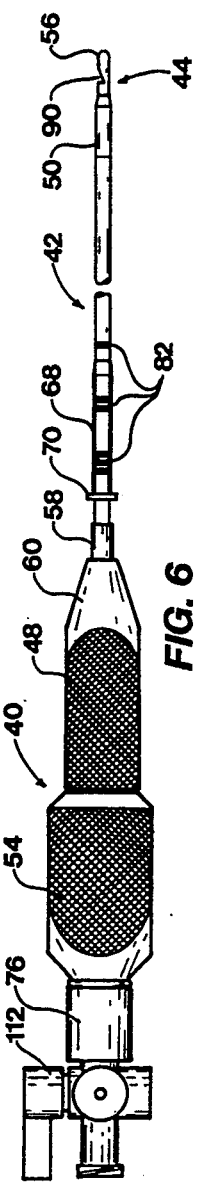
FIG. 6 is a side elevation view of a biopsy catheter constructed in accordance with the present invention shown with a cutting portion of the catheter exposed.

A proximal end of the outer tube 46 is connected to a connection member 58. The connection member 58 is fixedly attached to the outer tube 46 and to the outer tube handle 48 using an attachment means such as a shrink fit or an adhesive. Alternately this connection may be made using mating threads or fasteners. The outer tube handle 48 is formed of a rigid material such as hard plastic and is sized and shaped for manipulation by an operator's thumb and index finger. As such, the outer tube handle 48 is formed as a generally rectangular shaped block having a conically shaped distal end 60. As shown in FIGS. 5 and 6, the surface of the outer tube handle 48 may be textured or knurled to facilitate handling by an operator.

A distal end of the outer tube 46 is threaded with an internal thread 62. The cutter tip 50 of the outer tube assembly 42 is formed with a mating external thread 64 for connecting the cutter tip 50 to the outer tube 46. Alternately (or in conjunction) other thread arrangements and other fastening means such as an adhesive may be utilized to connect the cutter tip 50 to the outer tube 46.

The outer tube 46 may also include one or more length markers 82 formed on the outside diameter thereof. These length markers 82 enable the location of the biopsy catheter within an artery to be ascertained using techniques and equipment that are known in the art.

The cutter tip 50 is generally cylindrical in shape and has open ends. The cutter tip 50 is formed with a conical or tapered distal portion that terminates in a sharpened circumferential edge 66. This is the cutting edge of the biopsy catheter 40. The outside diameter of the cutter tip 50 is sized to enable passage through an artery. In general, the cutter tip 50 has the largest diameter of the portion of the biopsy catheter 40 which is placed into a patient's artery. The dimensioning of the outside diameter of the cutter tip 50 is thus critical in sizing a biopsy catheter 40 for a particular patient. As an example, different sized biopsy catheters may be used for pediatric, adolescent, and adult patients.

The inside diameter of the cutter tip 50 is sized slightly larger (e.g. 0.002 inches) than the outside diameter of the suction tip 56 of the inner tube 52. The cutter tip 50 can thus be slid over the suction tip 56 by manipulation of the outer tube handle 48 allowing the sharpened circumferential edge 66 of the cutter tip 50 to cut a tissue sample held in the suction tip 56. The cutter tip 50 is preferably formed of a relatively hard material such as stainless steel.

A cylindrical sleeve 68 is slidably mounted to the outer tube 46. The sleeve 68 includes a flanged portion 70. In use, the sleeve engages the entrance aperture of an introducer sheath (100 FIG. 9) and provides a reduced friction passage for sliding the outer tube 46 during the cutting step of the procedure. The flanged portion 70 of the sleeve 68 limits the penetration of the sleeve 68 into the introducer sheath (100 FIG. 9).

The inner tube 52 is slidably mounted within the outer tube 46 and may be formed of a flexible polymeric material such as teflon, nylon, or polyurethane. As with the outer tube 46 the inner tube 52 must be flexible enough to allow passage through the tortuous path of an artery but rigid enough to transmit compressive and tensile forces linearly from the inner tube handle 54 to the suction tip 56. Alternately the inner tube 52 and outer tube 46 may be formed of different polymeric material suitable to their particular function.

A proximal end of the inner tube 52 is connected to the inner tube handle 54 using an attachment means such as an adhesive. Alternately (or in conjunction) other fastening means such as mating threads or fasteners may be utilized to connect the inner tube 52 to the inner tube handle 54. The inner tube 52 passes through an opening 72 formed in the outer tube handle 48.

The inner tube 52 is reinforced with a larger diameter reinforcing tube 74 adjacent to its proximal end. The outer tube handle 48 is slidable over this larger diameter reinforcing tube 74. The inner tube handle 54 is formed as a generally rectangular shaped block sized for manipulation by the operator. The inner tube handle 54 is slightly larger than the outer tube handle 48 and may also have a textured or knurled surface. The inner tube handle 54 is adapted to be manipulated between the thumb and index finger of the operator to navigate the outer tube 46 through an artery and to slide the inner tube 52 with respect to the outer tube 46. A tube fitting 76 is connected to a proximal end of the inner tube handle 54 in fluid communication with an inside diameter of the inner tube 52 for connection to a stopcock 112 which is connected to a vacuum source (122 FIG. 10). This allows a vacuum to be directed through the inside diameter of the inner tube 52 and to the suction tip 56 of the inner tube 52. The vacuum being directed through the inner tube 52 of the biopsy catheter 40 from stopcock 112 to suction tip 56.

A distal end of the inner tube 52 is threaded with an internal thread 78. The suction tip 56 of the inner tube is formed with a mating external thread 80 at its proximal end for connecting the suction tip 56 to the inner tube 52. Alternately (or in conjunction) other fastening means such as an adhesive may be utilized to connect the suction tip 56 to the inner tube 52. The distal end of the suction tip 56 is closed and air tight (i.e. hermetically closed) and formed with a rounded or hemispherically shaped surface. The distal end of the suction tip 56 may also be radiopaque.

Figure 7:
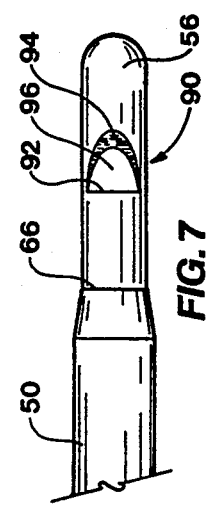
FIG. 7 is an enlarged view of the distal portion of the inner tube of a catheter constructed in accordance with the invention showing the beveled opening formed in the inner tube.
Figure 8:
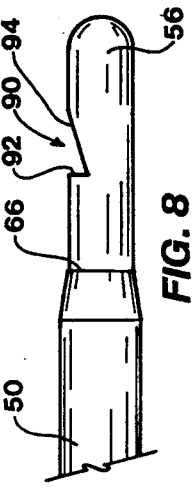
FIG. 8 is a side elevation view of FIG. 7.

With reference to FIGS. 7 and 8, a beveled opening 90 is formed in the suction tip 56 of the inner tube 52 for holding a tissue sample from the artery. The beveled opening 90 is located along an outer circumferential surface of the suction tip 56 and is in fluid communication with the inside diameter of the inner tube 52. As shown in FIG. 8, the beveled opening 90 is formed by the intersection of an end surface 92 situated generally perpendicular to a longitudinal axis of the suction tip 56 and a beveled surface 94 situated at an angle to a longitudinal axis of the suction tip 56. This forms an aperture 96 to the inside diameter of the inner tube 52. The depth of the end surface 92 is determined by the thickness of the wall of the suction tip 56 and by the angle of the beveled surface 94. This depth ultimately determines the thickness of the tissue sample and the depth of a cut into the artery. The size and depth of the beveled opening 90 can be selected to penetrate into a particular layer of the artery (i.e. inner layer 18, muscular layer 20, outer layer 22), and for obtaining a particular tissue sample.

With this arrangement an area of the artery contacted by an outer periphery of the beveled opening 90 is larger than the size of the aperture 96 of the suction tip 56. A tissue sample can thus be held in the beveled opening 90 by a vacuum directed through the inside diameter of the inner tube 52 but will not pass through the aperture 96 to the inside diameter of the inner tube 52.

Referring now to FIGS. 5 and 6, the biopsy catheter 40 is shown with the suction tip 56 in two different positions. As shown in FIG. 5, the outer tube handle 48 can be separated with respect to the inner tube handle 54 by the operator. This moves the cutter tip 50 over the suction tip 56 and covers the suction tip 56. In this position the cutting portion of the catheter is completely covered for insertion into and retraction from the artery.

As shown in FIG. 6, the suction tip 56 of the inner tube 52 can be extended outside of the cutter tip 50. In its extended position the suction tip 56 is situated for contacting the arterial wall. In the extended position vacuum directed through the beveled opening 90 will draw arterial tissue into contact with the opening 90. In the full extended position of the suction tip 56 the outer tube handle 48 is in contact with the inner tube handle 54. Conversely, by separating the outer tube handle 48 relative to the inner tube handle 54, the cutting edge 66 of the cutter tip 50 moves over the beveled opening 90 to sever arterial tissue in contact with the beveled opening 90.

Figure 9:
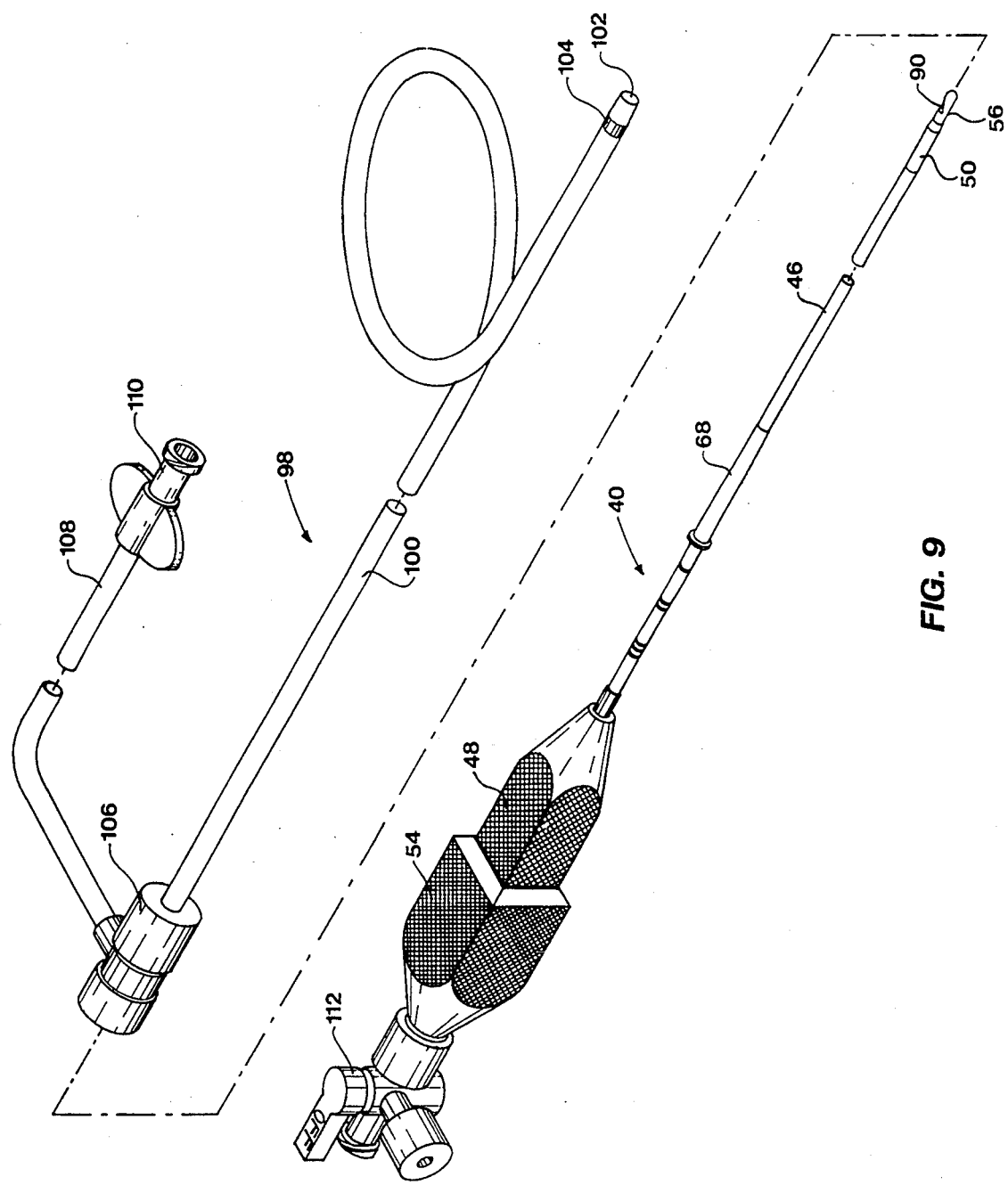
FIG. 9 is a perspective view of a biopsy catheter constructed in accordance with the present invention and an introducer sheath, bent into the desired conformation, and modified by the addition of a radiopaque marker at the distal portion of the sheath, and showing the manner in which they are used with respect to each other.

With reference to FIG. 9, the biopsy catheter 40 is used in conjunction with an introducer sheath assembly 98 which has been modified in accordance with the invention. As will be more fully explained, the introducer sheath assembly 98 includes a stiff introducer sheath 100 that is adapted to be placed within an artery and guided to a desired location in the artery using techniques which are known in the art. The introducer sheath 100 provides a conduit for operating the biopsy catheter 40 of the invention within the vascular system. As will be more fully explained, in use of the biopsy catheter 40 only the cutter tip 50 and suction tip 56 of the biopsy catheter 40 extend past the open distal end 102 of the introducer sheath 100 for contacting the arterial wall.

The introducer sheath 100 may be bent into a configuration that matches the arterial path where it will ultimately be located within the vascular system. A radiopaque marker 104 is located adjacent to the open distal end 102 for locating the introducer sheath 100 within the vascular system. The introducer sheath assembly 98 also includes a housing 106 coupled to a conduit 108.

The housing 106 contains an internal membrane seal. A tube fitting 110 is connected to the conduit 108. The conduit 108 may be used to inject (or evacuate) various fluids into the vascular system.

As also shown in FIG. 9, the inner tube handle 54 of the biopsy catheter 40 is attached to a stopcock 112 using the tube fitting 76 (FIG. 4) on the inner tube handle 54. The stopcock 112 is formed as a manually operable three way valve. The stopcock 112 may be used to direct various fluid flows into and out of the inner tube 52 of the biopsy catheter 40. Moreover, multiple stopcocks 112 and 114 may be combined in series to control the vacuum flow and for directing various fluid flows through the biopsy catheter.

Figure 10:
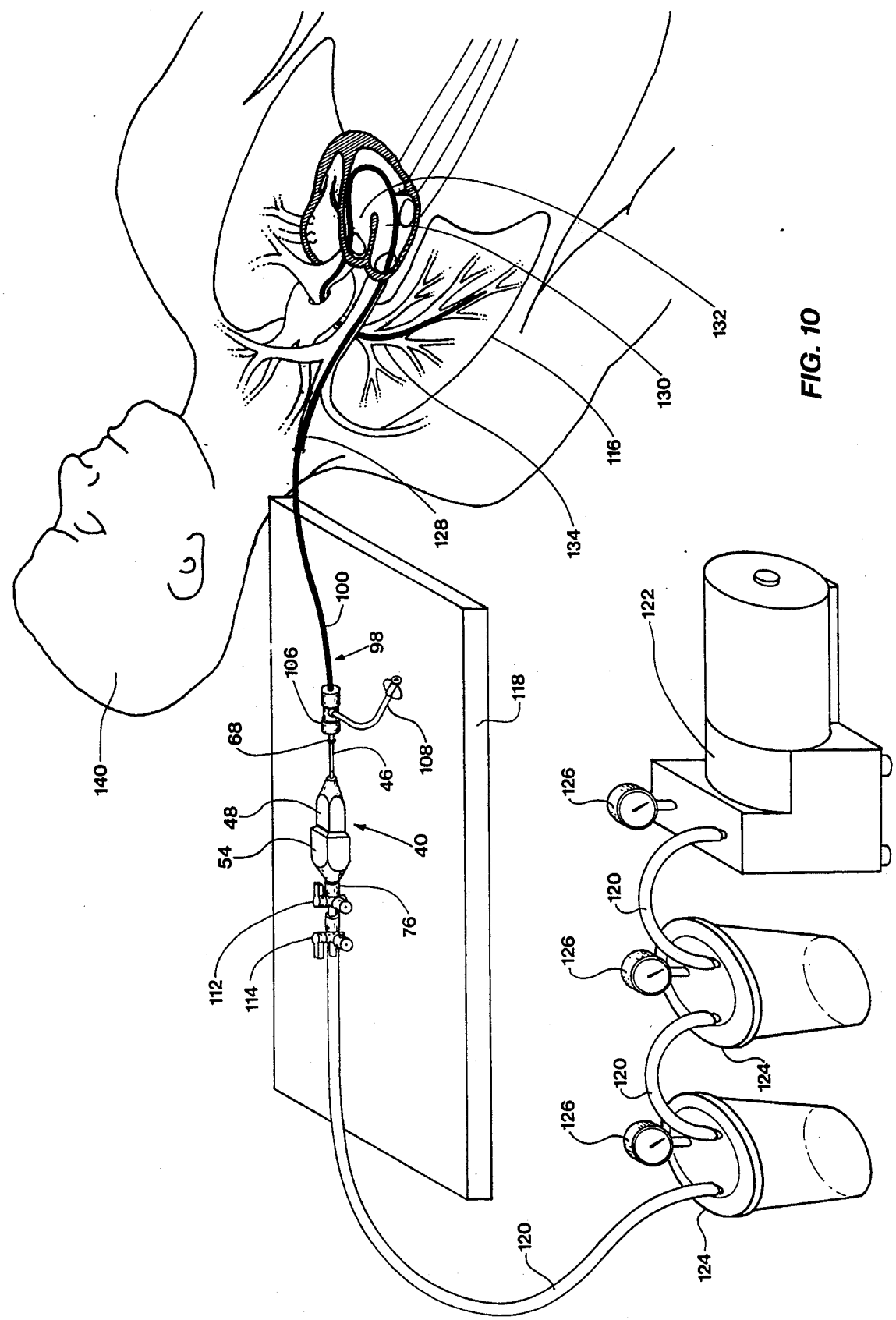
FIG. 10 is an isometric view of the complete operating room configuration necessary to perform a biopsy procedure in a pulmonary artery including an introducer sheath, a biopsy catheter constructed in accordance with the present invention, stopcocks, connective tubing, suction canisters, vacuum gauges, and a vacuum source.

Referring now to FIG. 10, the method of the invention is illustrated for obtaining a biopsy sample from a patient 114. In the illustrated procedure the biopsy sample is to be obtained from one of the pulmonary arteries of the patients right lung 116. The patient 114 is situated in a reclining position adjacent to a support table 118 for the arterial biopsy catheter 40 and introducer sheath 100.

FIG. 10 depicts a point of the procedure wherein the outer tube of the biopsy catheter 40 has been placed within the introducer sheath 100 and located at a desired location within the patient's vasculature. At this point in the procedure the biopsy catheter 0 is supported on the support table 118 with the inner tube handle 54 and outer tube handle 48 placed together as previously shown in FIG. 6.

In addition, the tube fitting 76 on the inner tube handle 54 has been connected to a pair of stopcocks 112 and 114. The stopcocks 112 and 114 are in fluid communication with the inner tube 52 (FIG. 4) of the biopsy catheter 40 for regulating fluid flow through the inner tube 52. The stopcocks 112 and 114 are also in fluid communication with a vacuum tube 120 coupled to a vacuum source 122 such as a vacuum pump. A pair of vacuum canisters 124 are connected to the vacuum tube 120 and to the vacuum source 122. Each of these components also includes a pressure gauge 126.

Figure 11:
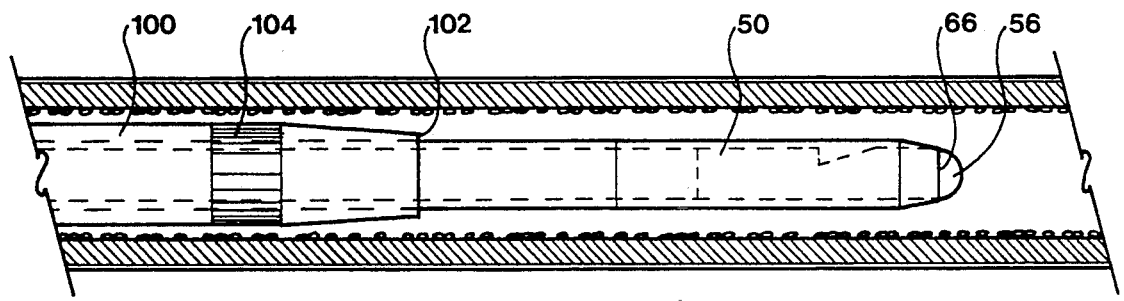
FIG. 11 is an enlarged view of a biopsy catheter being introduced into an artery with the distal portion of the inner tube covered by the distal portion of the outer tube.
Figure 12:
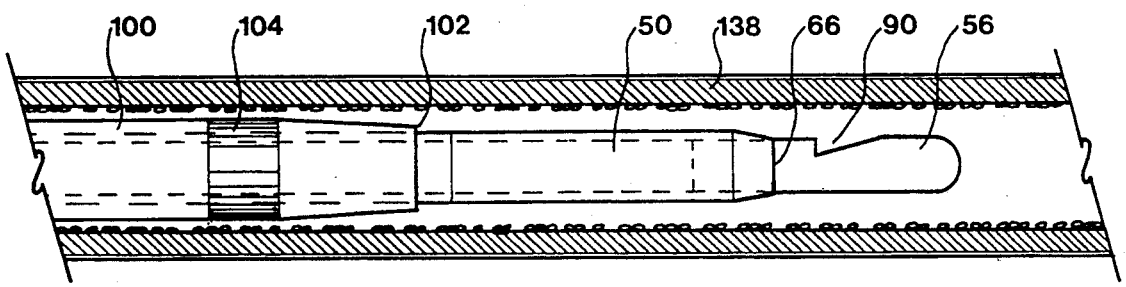
FIG. 12 is an enlarged view of a biopsy catheter in an artery with the distal portion of the outer tube retracted over the distal portion of the outer tube retracted over the distal portion of the inner tube, exposing the beveled opening in the inner tube.

Referring now to FIGS. 10–15, the procedure for obtaining a biopsy sample in accordance with the invention, stated in detail, is as follows:

1. Initially the patient 140 is prepared for a cardiac catheterization.
2. Access to the desired biopsy site can be via the internal jugular vein 128 or alternately the femoral vein.
3. The desired vein can be accessed percutaneously with a needle of a suitable size, for example an 18 gauge Courand-Style Needle (with obturator), Universal Medical Instrument Corporation, Part #4502-13-1518 (not shown).
4. A straight fixed core guidewire of suitable size is then passed through the lumen of the needle, and the needle is then removed, leaving the guidewire in the vein (not shown).
5. A short introducer sheath with dilator is then threaded over the guidewire into the vein for example, a Hemaquet 9F Arterial/Venous Percutaneous Catheter Introducer Set, USCI Angiographic Systems Division, C. R. Bard, Inc., containing: 1 9F sheath, 1 9F dilator, and 1 0.038" straight fixed Core Guide Wire, Part #008344, U.S. Pat. No. 4,424,833 (not shown).
6. The guidewire is then removed, followed by the dilator leaving the short sheath introducer with hemostatic access to the desired vein (not shown).
7. In this example, biopsy specimens are desired from the pulmonary arteries located in the right lung. To access the desired location in the vasculature, an endhole catheter, for example a 7F, 110 cm Balloon Wedge Pressure Catheter, Arrow International, Inc., Part #AI-07127 (not shown) is floated through the right atrium 130, and the right ventricle 132 to a pulmonary artery 134 and then to the desired branch in the pulmonary arterial tree.
8. A stiff guidewire, for example, an Amplatz Super Stiff ST-1 Guidewire, 0.038 in diameter, 260 cm length, Medi-Tech, Boston Scientific Corporation, Part #46-510 (not shown) after being bent into the proper configuration, is passed through the endhole catheter (not shown).
9. The endhole catheter (not shown) is then removed while the position of the stiff guidewire is maintained.
10. The stiff introducer sheath 100 and a dilator, for example, a Check-Flow II ™ Blue Mullins Introducer Set, 9.0 French Introducer Sheath and Dilator, Part #RCF-9-038-75-MTS, U.S. Pat. No. 5,006,113 (not shown) are then threaded over the stiff guidewire (not shown). The introducer sheath 100 has been specifically adapted for the invention by adding the radiopaque marker 104 (FIG. 9) and bending it into the desired configuration. The introducer sheath 100 remains in place while the stiff guidewire (not shown) and dilator (not shown) are removed.
11. An angiographic catheter, for example a 7F Berman Angiographic Balloon Catheter, Arrow International, Inc. Part #AI-07132 (not shown) is then delivered to the desired site through the introducer sheath 100 and an angiogram is performed by injecting contrast solution with simultaneous fluoroscopy. This angiogram illuminates and records the area of vasculature of interest.
12. The angiographic catheter (not shown) is then removed and the biopsy catheter 40 is introduced to the desired site through the introducer sheath 100. The desired relationship between the biopsy catheter 40 and the introducer sheath is achieved when the suction tip 56 and cutting tip 50 of the biopsy catheter 40 clear the open end 102 of the introducer sheath 100. This is shown in FIG. 11. During this step, the suction tip 56 and cutting tip 50 (i.e. the cutting portion of the biopsy catheter 40) are aligned in the closed configuration, as shown in FIG. 11, to enable easier passage through the bends and curves of the introducer sheath 100. The stopcock 112 on biopsy catheter 40 is closed to prevent fluid flow during this step.
13. Upon further fluoroscopic visualization of the biopsy catheter 40 and radiopaque marker 104 on the introducer sheath 100, the biopsy catheter 40 is positioned to the desired area and the cutting portion of the biopsy catheter is opened as shown in FIG. 12. In this position the inner tube handle 54 and outer tube handle 48 are together.
14. With the suction tip 56 and cutting tip 50 in the open position the beveled opening 90 on the suction tip 56 is exposed. The cutting tip 50 is retracted to expose the beveled opening 90.

Figure 13:
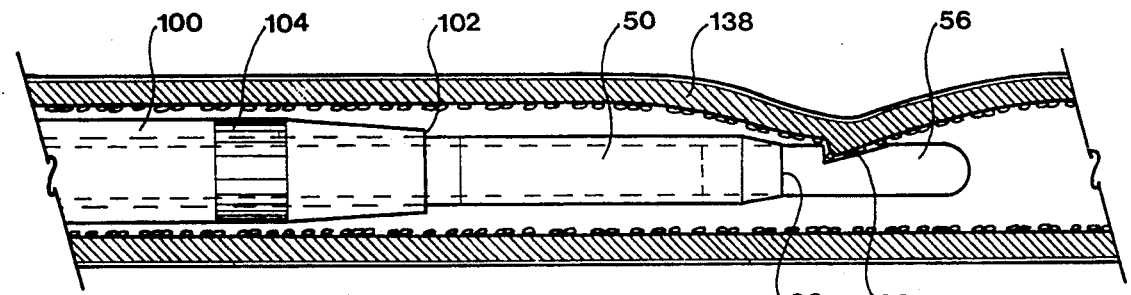
FIG. 13 is an enlarged view of a biopsy catheter in an artery with the distal portion of the outer tube retracted over the distal portion of the inner tube, with the beveled opening in the inner tube contacting the inner surface of the arterial wall.
Figure 14:
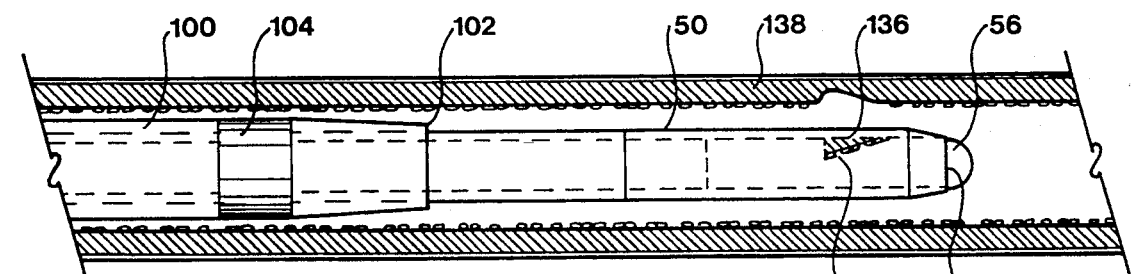
FIG. 14 is an enlarged view of a biopsy catheter in an artery with a portion of the artery cut by the distal sharpened edge of the outer tube and held within the beveled opening of the inner tube.
Figure 15:
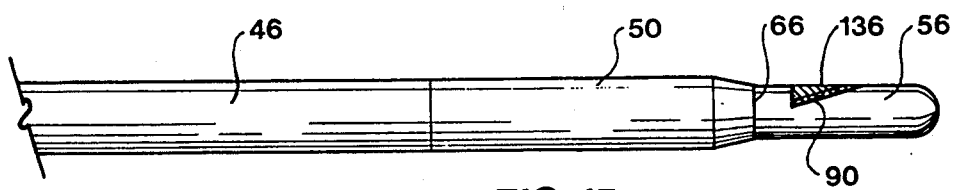
FIG. 15 is an enlarged view of the distal portion of a biopsy catheter removed from the patient and the introducer sheath with the outer tube retracted from the inner tube, revealing a biopsy specimen from the inner surface of an arterial wall held in the beveled opening of the inner tube.

15. Once the desired location is achieved, the vacuum system is evacuated up to the stopcock 114 at the distal end of vacuum tubing 120.
16. Once a full vacuum is established (approximately 29.5 in Hg vacuum), according to vacuum gauges 126, both stopcocks 114 and 112 are opened transmitting the vacuum through the inner tube handle 54 through the inner tube 52 to the beveled opening 90 of the suction tip 56. This draws endoarterial tissue from the arterial wall 138 into the beveled opening 96 of the suction tip 56. This is shown in FIG. 13.
17. In preparation for making the biopsy cut, the cylindrical sleeve 68 (FIG. 10) is then slid over the outer tube 46 into a membrane seal in the introducer sheath housing 106 (FIG. 10). This is done so that the outer tube 46 of the biopsy catheter is free to move without being hindered by the membrane seal.
18. While the inner tube handle 54 is held steady by a co-operator, the physician holds the introducer sheath housing 106 steady and initiates the cutting action by advancing the outer tube handle 48 relative to the inner tube handle 54 and introducer sheath housing 106. In this manner, the cutter tip 50 is advanced over the beveled opening 90 of the suction tip 56 severing the biopsy sample 136 from the arterial wall 138. This is shown in FIG. 14.
19. After the cut has been made, stopcocks 112 and 114 are closed, the vacuum source 122 is shut off, and the vacuum is released from within the vacuum line 120 and the vacuum canisters 124 by turning stopcock 114. The entire biopsy catheter 40 is then removed from the introducer sheath 100 with an initial sharp tug to completely sever the biopsy sample 136 from the arterial wall 138.
20. The biopsy catheter is removed with the suction tip 56 and cutting tip 50 in the closed position and with the suction tip 56 containing the biopsy sample 136 within the beveled opening 90. The biopsy sample 136 is protected by the cutting tip 50 when the biopsy catheter 40 is in the closed configuration (FIG. 14). The orientation of the biopsy sample 136 with respect to its parent tissue is also preserved.
21. The biopsy catheter 40 is completely removed from the patient and the cutter tip 50 is retracted from the suction tip 56 revealing the biopsy specimen 136 captured within the beveled opening 90. This is shown in FIG. 15.
22. The biopsy sample 136 is removed from the beveled opening 90 with a sterile needle (not shown) and is placed in a sterile container (not shown) for such future uses as histological examination, cell culture, diagnostic, therapeutic, or other uses.
23. Upon flushing the biopsy catheter 40 with sterile saline solution, the catheter is inspected, and if undamaged, is reintroduced into the patient to take additional biopsy specimens as desired.

Thus, the invention provides a simple yet unobvious method and apparatus for obtaining a biopsy sample from the inner layers of an arterial wall. While the method of the invention has been described with reference to a preferred embodiment thereof, as will be apparent to those skilled in the art, therefore certain changes and modifications can be made without departing from the scope of the invention as defined by the following claims.

What is claimed is:

1. A method for obtaining a biopsy sample from an inner surface of an arterial wall, comprising:
    inserting a flexible catheter having an opening into the artery and positioning the opening at a segment of the artery without localized stenosis;
    initiating contact between tissue on an inner surface of the arterial wall and an outer periphery of the opening;
    cutting a biopsy sample from the tissue in contact with the outer periphery of the opening;
    retaining the biopsy sample within the opening formed in the catheter; and
    withdrawing the catheter from the artery with the retained biopsy sample.

2. The method of obtaining a biopsy sample as recited in claim 1 and wherein an orientation of the biopsy sample is preserved as the catheter is withdrawn.

3. The method of obtaining a biopsy sample as recited in claim 1 and wherein the biopsy sample includes elastic tissue.

4. The method of obtaining a biopsy sample as recited in claim 1 and further comprising protecting the retained biopsy sample as the catheter is withdrawn.

5. A method for obtaining a biopsy sample from an artery comprising:
    inserting a hollow catheter into the artery said catheter including an opening having an outer periphery;
    positioning the opening of the catheter at a segment of the artery without localized stenosis;
    initiating contact between an inner surface of the artery and the outer periphery of the opening by directing a vacuum through the catheter to the opening and drawing arterial tissue into the opening;
    cutting a biopsy sample from the tissue and retaining the biopsy sample within the opening; and
    withdrawing the catheter from the artery with the retained biopsy sample.

6. A method of obtaining a biopsy sample as claimed in claim 5 and wherein the segment of the artery without localized stenosis is a non-stenotic segment.

7. A method of obtaining a biopsy sample as claimed in claim 5 and wherein the segment of the artery without localized stenosis has generalized stenoses.

8. A method for obtaining a biopsy sample as claimed in claim 5 and wherein the biopsy sample contains cells selected from the group of cells consisting of endothelial cells, smooth muscle cell and adventitia cells.

9. A method for obtaining a biopsy sample as claimed in claim 5 and wherein the opening is formed with a beveled periphery and a size and depth of the beveled periphery are selected to initiate contact with a particular layer of the artery.

10. A method for obtaining a biopsy sample as claimed in claim 5 and wherein the biopsy sample contains a material selected from the group of materials consisting of hypertrophied tissue, thickened tissue, neoplastic tissue, bacterial conglomerations, virally infected cells, inflammatory cells, and cells containing exogenously introduced recombinant genetic material.

11. A method for obtaining a biopsy sample from an arterial wall comprising:
    inserting a flexible catheter into the artery said catheter including an opening formed in the catheter with a beveled peripheral surface in flow communication with a vacuum source, said catheter further including a cutting edge adapted to slide over said opening;

positioning the opening at a segment of the artery without localized stenoses;

directing a vacuum through the opening to draw an inner surface of the artery into the opening and into contact with the beveled peripheral surface of the opening;

cutting a biopsy sample from the artery by sliding the cutting edge over the opening to sever tissue from the artery; and withdrawing the catheter from the artery with the biopsy sample retained within the opening.

12. The method for obtaining a biopsy sample as recited in claim 11 and wherein the opening is formed in a sidewall of the catheter and has a beveled surface.

13. The method for obtaining a biopsy sample as recited in claim 12 and wherein the opening is formed in an inner tube of the catheter and the cutting edge is formed in an outer tube slidably mounted on the inner tube.

14. The method for obtaining a biopsy sample as recited in claim 13 and wherein the outer tube is positioned to protect the biopsy sample retained in the opening during withdrawal of the catheter from the body.

15. The method for obtaining a biopsy sample as recited in claim 11 and further comprising identifying an orientation of the biopsy sample relative to parent tissue in the artery using a placement of the biopsy sample in the opening.

16. The method for obtaining a biopsy sample as recited in claim 11 and further comprising forming the beveled peripheral surface for retaining a biopsy sample having a predetermined thickness.

17. A method for obtaining a biopsy sample from an artery of a patient comprising the steps of:

inserting an introducer sheath with a radiopaque marker at its distal end into an artery of the patient;

using the radiopaque marker to position the introducer sheath at a desired segment of the artery;

inserting a flexible biopsy catheter into the introducer sheath said biopsy catheter including an opening;

initiating contact between an outer periphery of the opening and tissue on an inner surface of the artery;

cutting a biopsy sample from the tissue in contact with the outer periphery of the opening;

retaining the biopsy sample within the opening; and withdrawing the catheter from the body.

18. The method for obtaining a biopsy sample as recited in claim 17 and further comprising forming the opening as a beveled opening with a beveled surface adapted to retain a biopsy sample having a predetermined thickness.

19. The method for obtaining a biopsy sample as recited in claim 17 and wherein the biopsy sample includes elastic tissue.

20. The method for obtaining a biopsy sample as recited in claim 17 and wherein a cylindrical sleeve is placed around said outer tube to provide a reduced friction passage between said introducer sheath and said outer tube.

* * * * *

UNITED STATES PATENT AND TRADEMARK OFFICE
CERTIFICATE OF CORRECTION

PATENT NO. : 5,406,959
DATED : April 18, 1995
INVENTOR(S) : David Mann

It is certified that error appears in the above-indentified patent and that said Letters Patent is hereby corrected as shown below:

On the title page item [54], change "DIAGNOSTING" to --DIAGNOSING--

In col 1, line 3, change "diagnosting" to --diagnosing--

Signed and Sealed this

Nineteenth Day of September, 1995

Attest:

BRUCE LEHMAN

Attesting Officer     Commissioner of Patents and Trademarks